United States Patent
Yoshida et al.

(10) Patent No.: US 12,018,281 B2
(45) Date of Patent: Jun. 25, 2024

(54) CARDIOMYOCYTE MATURATION PROMOTER

(71) Applicants: Kyoto University, Kyoto (JP); Takeda Pharmaceutical Company Limited, Osaka (JP)

(72) Inventors: Yoshinori Yoshida, Kyoto (JP); Kenji Miki, Kyoto (JP); Shigeru Kondo, Kanagawa (JP)

(73) Assignees: Kyoto University, Kyoto (JP); Takeda Pharmaceutical Company Limited, Osaka (JP)

( * ) Notice: Subject to any disclaimer, the term of this patent is extended or adjusted under 35 U.S.C. 154(b) by 933 days.

(21) Appl. No.: 17/042,635

(22) PCT Filed: Mar. 28, 2019

(86) PCT No.: PCT/JP2019/013530
§ 371 (c)(1),
(2) Date: Sep. 28, 2020

(87) PCT Pub. No.: WO2019/189554
PCT Pub. Date: Oct. 3, 2019

(65) Prior Publication Data
US 2021/0009956 A1    Jan. 14, 2021

(30) Foreign Application Priority Data

Mar. 30, 2018  (JP) ................................ 2018-069871

(51) Int. Cl.
C12N 5/077  (2010.01)
C12N 15/113  (2010.01)

(52) U.S. Cl.
CPC .......... *C12N 5/0657* (2013.01); *C12N 15/113* (2013.01)

(58) Field of Classification Search
CPC ................. C12N 5/0657; C12N 15/113; C12N 2500/02; C12N 2500/24; C12N 2501/115; C12N 2501/155; C12N 2501/16; C12N 2501/727; C12N 2501/999; C12N 2506/45; C12N 2533/90; A61K 35/34
See application file for complete search history.

(56) References Cited

U.S. PATENT DOCUMENTS

| | | |
|---|---|---|
| 2003/0065023 A1 | 4/2003 | Swindell et al. |
| 2005/0101647 A1 | 5/2005 | Oda et al. |
| 2007/0010012 A1 | 1/2007 | Gold et al. |
| 2007/0293465 A1 | 12/2007 | Shenk et al. |
| 2008/0153899 A1 | 6/2008 | Swindell et al. |
| 2008/0182871 A1 | 7/2008 | Lee et al. |
| 2009/0143376 A1 | 6/2009 | Milburn et al. |
| 2011/0104122 A1 | 5/2011 | Yamashita et al. |
| 2012/0029012 A1 | 2/2012 | Lee et al. |
| 2013/0079306 A1 | 3/2013 | Uchida et al. |
| 2015/0284684 A1 | 10/2015 | Gold et al. |
| 2016/0122718 A1 | 5/2016 | Braam |
| 2016/0271183 A1 | 9/2016 | Hajjar et al. |
| 2017/0159018 A1 | 6/2017 | Braam et al. |
| 2019/0203179 A1* | 7/2019 | Porrello ............. C12Q 1/025 |

FOREIGN PATENT DOCUMENTS

| | | |
|---|---|---|
| CN | 101254191 A | 9/2008 |
| EP | 1 460 067 A1 | 9/2004 |
| JP | 2016-521571 A | 7/2016 |
| JP | 2017-060422 A | 3/2017 |
| WO | WO-92/16486 A1 | 10/1992 |
| WO | WO-02/076402 A2 | 10/2002 |
| WO | WO-03/045929 A1 | 6/2003 |
| WO | WO-2006/094235 A1 | 9/2006 |
| WO | WO-2007/002136 A2 | 1/2007 |
| WO | WO-2008/063548 A2 | 5/2008 |
| WO | WO-2009/118928 A1 | 10/2009 |
| WO | WO-2012/002527 A1 | 1/2012 |

OTHER PUBLICATIONS

Hong et al. "Cardiac BIN1 folds T-tubule membrane, controlling ion flux and limiting arrhythmia" Nat Med. Jun. 2014;20(6):624-32 . . . (Year: 2014).*

Baxter et al., "Discovery and Synthesis of Methyl 2,5-Dimethyl-4-[2-(phenylmethyl)benzoyl]-1H-pyrrole-3-carboxylate (FPL 64176) and Analogues: The First Examples of a New Class of Calcium Channel Activator," J. Med. Chem., 1993, 36:2739-2744.

Clements et al., "High-Throughput Multi-Parameter Profiling of Electrophysiological Drug Effects in Human Embryonic Stem Cell Derived Cardiomyocytes Using Multi-Electrode Arrays," Toxicological Sciences, 2014, 140(2):445-461.

Kang et al., "Ca2 Channel Activators Reveal Differential L-Type Ca2 Channel Pharmacology between Native and Stem Cell-Derived Cardiomyocytes," The Journal of Pharmacology and Experimental Therapeutics, 2012, 341(2):510-517.

(Continued)

*Primary Examiner* — Titilayo Moloye
(74) *Attorney, Agent, or Firm* — Foley & Lardner LLP

(57) ABSTRACT

The present invention provides a cardiomyocyte maturation promoter.

The present invention provides a cardiomyocyte maturation promoter comprising one or more compounds selected from 2-methoxy-5-((Z)-2-(3,4,5-trimethoxyphenyl)vinyl)phenol,
(1-ethyl-1H-benzotriazol-5-yl)methyl (2-(2-methoxy-4-methylphenyl)-4-methyl-1,3-thiazol-5-yl)carbamate,
(2'beta)-22-oxovincaleukoblastine,
2-(2-(4-chlorophenyl)ethyl)-6-(2-furyl)-3H-imidazo[4,5-b]pyridine,
4,5-anhydro-1,2-dideoxy-4-methyl-2-((N-(morpholin-4-ylacetyl)-L-alanyl-O-methyl-L-tyrosyl)amino)-1-phenyl-L-threo-pent-3-ulose,
3-(3-methoxyphenyl)-N7,N7-dimethylisoquinoline-1,7-diamine,
methyl 4-(2-benzylbenzoyl)-2,5-dimethyl-1H-pyrrole-3-carboxylate,
2'-(4-aminophenyl)-1H,1'H-2,5'-bibenzimidazol-5-amine, and salts thereof.

2 Claims, 1 Drawing Sheet
Specification includes a Sequence Listing.

(56) References Cited

OTHER PUBLICATIONS

Laflamme et al., "Cardiomyocytes derived from human embryonic stem cells in pro-survival factors enhance function of infarcted rat hearts", Nature Biotechnology, Sep. 2007, 25(9):1015-1024.

Rast et al., "An integrated platform for simultaneous multi-well field potential recording and Fura-2-based calcium transient ratiometry in human induced pluripotent stem cells (hiPSC)-derived cardiomyocytes," Journal of Pharmacological and Toxicological Methods, Apr. 25, 2015, 75:91-100.

Sun et al., "Bioengineering Approaches to Mature Human Pluripotent Stem Cell-Derived Cardiomyocytes," Frontiers in Cell and Developmental Biology, Mar. 9, 2017, 5(19):1-8.

Yan et al., "Cyclosporin-A potently induces highly cardiogenic progenitors from embryonic stem cells," Biochemical and Biophysical Research Communications, 2009, 379:115-120.

Yang et al., "Human cardiovascular progenitor cells develop from a KDR embryonic-stem-cell-derived population," Nature, May 22, 2008, 453(7194):524-528.

Zeng et al., "Response of human induced pluripotent stem cell-derived cardiomyocytes to several pharmacological agents when intrinsic syncytial pacing is overcome by acute external stimulation," Journal of Pharmacological and Toxicological Methods, Jan. 10, 2018, 91:18-26.

Zeng et al., "Use of FDSS/μCell Imaging platform for preclinical cardiac electrophysiology safety screening of compounds in human induced pluripotent stem cell-derived cardiomyocytes," Journal of Pharmacology and Toxicological Methods, May 21, 2016, 81:217-222.

Jaroch et al., "Combretastatins: In vitro structure-activity relationship, mode of action and current clinical status," Pharmacological Reports, 2016, 68:1266-1275.

Sakamoto et al., "Abstract 110: The Estrogen-related Receptor Gamma Promotes Maturation of iPSC-derived Cardiac Myocytes," Circulation Research, 2016, 119:A110.

Bird et al., "The human adult cardiomyocyte phenotype," Cardiovascular Research, May 1, 2003, 58(2):423-434.

CAS No. 2068-78-2, Vincristine sulfate, Oct. 2, 2011, http://www.chemnet.com/cas.id/2068-78-2/Vincristine-sulfate.html.

Pettit et al., "Antineoplastic Agents. 291. Isolation and Synthesis of Combretastatins A-4, A-5, and A-6," J. Med. Chem., Jan. 1, 1995, 38(10):1666-1672.

\* cited by examiner

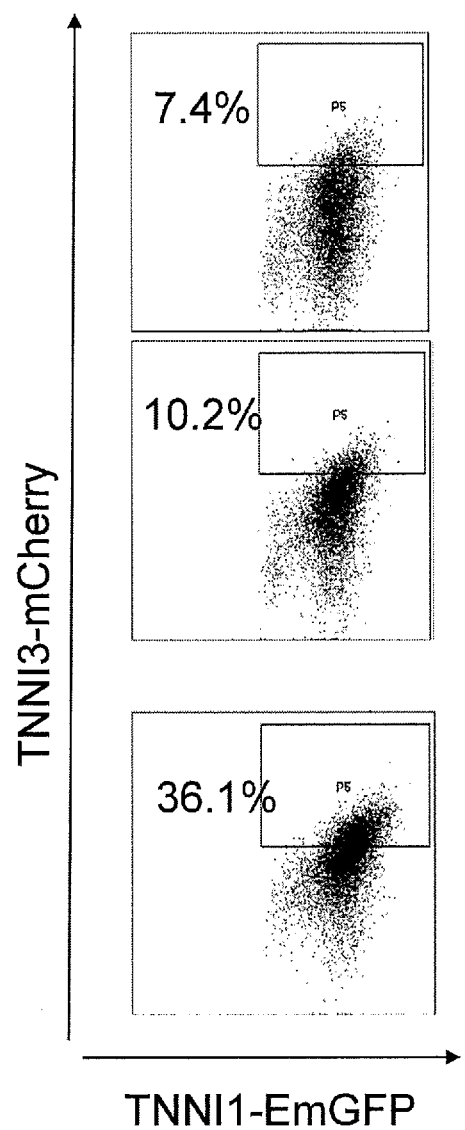

CARDIOMYOCYTE MATURATION PROMOTER

TECHNICAL FIELD

The present invention relates to a cardiomyocyte maturation promoter, and a preparation method of mature cardiomyocytes.

Background of the Invention

Cardiac diseases are the leading cause of death in the world. Cardiac transplantation, which is currently the sole therapeutic option for severe heart failure patients, suffers from donor shortage. A potential therapeutic option as an alternative to cardiac transplantation is transplantation of cardiomyocytes derived from pluripotent stem cells (e.g., iPS cells (induced pluripotent stem cells), ES cells (embryonic stem cells), etc.). The alternative option has been desired to be developed promptly. Moreover, cardiomyocytes derived from pluripotent stem cells (e.g., iPS cells, ES cells, etc.) are also required as cells used for drug toxicity tests and cardiac disease model studies.

Improvement of efficiency and safety is essential to apply iPS cell-derived mature cardiomyocytes to regenerative medicine. Regarding efficiency, there is a problem of low cost efficiency, because the number of cardiomyocytes capable of inducing maturation is small and proteins such as growth factors in a culture medium are very expensive. Regarding safety, there is a problem that cardiomyocytes have a low purity, and proliferative cells other than the cardiomyocytes can be contaminated, so that there is a risk of canceration.

Moreover, for drug toxicity tests and cardiac disease model studies using cardiomyocytes, it is necessary to collect a large number of mature cardiomyocytes that sufficiently mimic cardiomyocytes in the living body. Cardiomyocytes lose their division potential at the same time as the birth, and regeneration of those cells is very difficult. Because of such properties, a number of studies have been carried out for inducing differentiation of pluripotent stem cells into cardiomyocytes in order to obtain a large number of cardiomyocytes (Patent Document 1, Patent Document 2, Non-patent Document 1, Non-patent Document 2 and Non-patent Document 3).

However, in general, it is said that cardiomyocytes derived from human pluripotent stem cells stay in an immature stage similar to fetal cardiomyocytes, and that their ion channel function is insufficient compared to adult cardiomyocytes. Thus, for the purpose of screening of drug toxicity and therapeutic agents in relation to ion channels, mature cardiomyocytes are required to be used.

Therefore, mature cardiomyocytes and a preparation method thereof are required as cells used for cardiomyocyte transplantation and for screening of drug toxicity and therapeutic drug.

Patent Documents 3 to 9 and Non-Patent Document 4 disclose the following compounds.

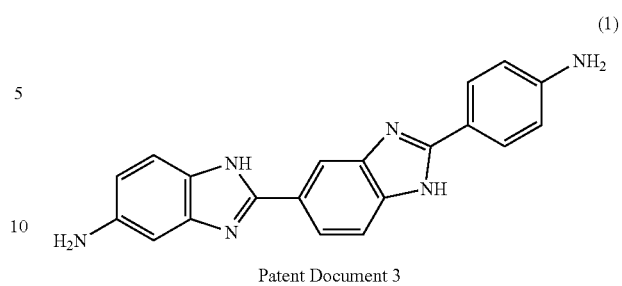

Patent Document 3

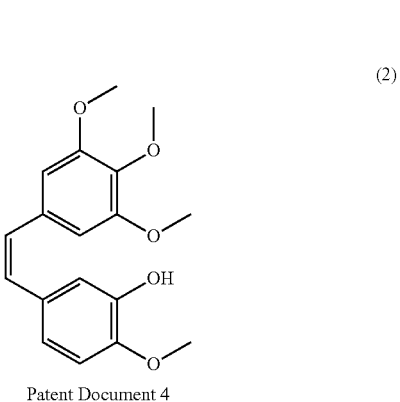

Patent Document 4

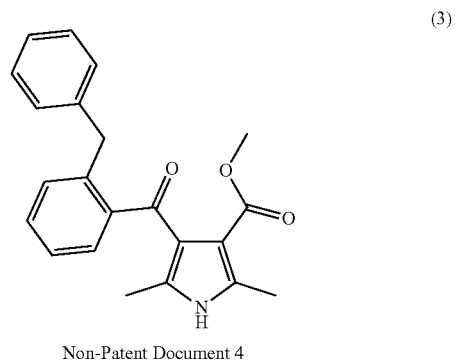

Non-Patent Document 4

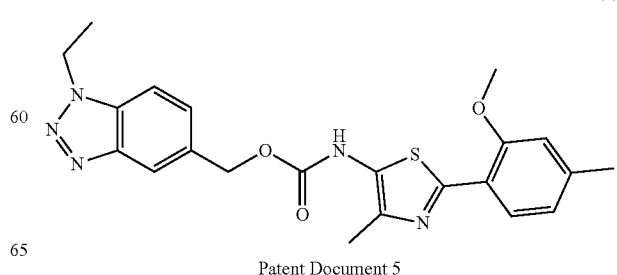

Patent Document 5

(5)

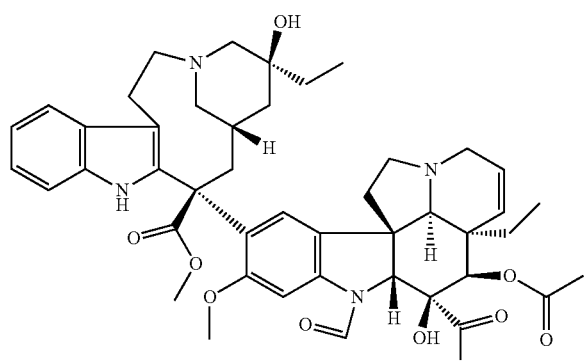

Patent Document 6

(6)

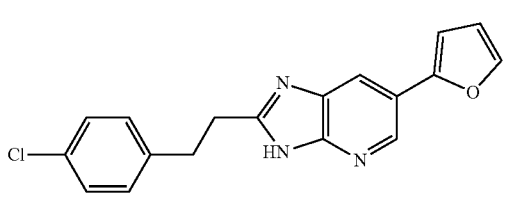

Patent Document 7

(7)

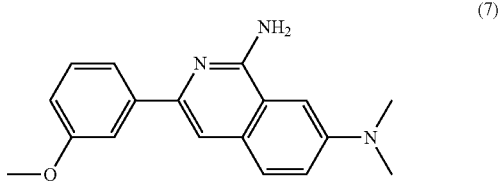

Patent Document 8

(8)

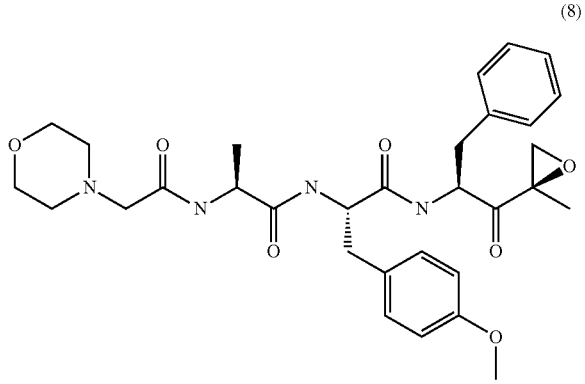

Patent Document 10 (a diastereomer of the below-mentioned Example Compound 5)

However, none of the documents disclose that the above-mentioned compounds have an activity to promote the maturation of a cardiomyocyte.

It is possible to obtain mature cardiomyocytes by culturing immature cardiomyocytes for a long period (for example, 1 year or more). However, as a commercial preparation method of mature cardiomyocytes, such method takes too much time and requires expensive medium and medium additive.

Therefore, development of a cardiomyocyte maturation promoter, which can efficiently prepare mature cardiomyocytes with high purity in a short period at low cost, is still desired.

DOCUMENT LIST

Patent Document

Patent Document 1: WO 2007/002136
Patent Document 2: WO 2009/118928
Patent Document 3: WO 2006/094235
Patent Document 4: WO 92/16486
Patent Document 5: WO 2012/002527
Patent Document 6: WO 02/076402
Patent Document 7: WO 03/045929
Patent Document 8: WO 2008/063548
Patent Document 9: US 2007/0293465

Non-Patent Document

Non-Patent Document 1: Yan P, et al, Biochem Biophys Res Commun. 379:115-20 (2009)
Non-Patent Document 2: Laflamme M A, et al, Nat Biotechnol, 25:1015-1024 (2007)
Non-Patent Document 3: Yang L et al, Nature, 453:524-528 (2008)
Non-Patent Document 4: Journal of Medicinal Chemistry, 1993, vol. 36, pp 2739-2744

SUMMARY OF THE INVENTION

Problems to be Solved by the Invention

The present invention aims to provide a cardiomyocyte maturation promoter, which can efficiently prepare mature cardiomyocytes with high purity in a short period at low cost.

Means of Solving the Problems

The present inventors have found that the following compounds or salts thereof have an activity to promote the maturation of a cardiomyocyte. As a result of further studies, they have completed the present invention.

Accordingly, the present invention is as follows.

[1] A cardiomyocyte maturation promoter comprising at least one compound selected from 2-methoxy-5-((Z)-2-(3,4,5-trimethoxyphenyl)vinyl)phenol, (1-ethyl-1H-benzotriazol-5-yl)methyl (2-(2-methoxy-4-methylphenyl)-4-methyl-1,3-thiazol-5-yl)carbamate, (2'beta)-22-oxovincaleukoblastine, 2-(2-(4-chlorophenyl)ethyl)-6-(2-furyl)-3H-imidazo[4,5-b]pyridine, 4,5-anhydro-1,2-dideoxy-4-methyl-2-((N-(morpholin-4-ylacetyl)-L-alanyl-O-methyl-L-tyrosyl)amino)-1-phenyl-L-threo-pent-3-ulose, 3-(3-methoxyphenyl)-N7,N7-dimethylisoquinoline-1,7-diamine, methyl 4-(2-benzylbenzoyl)-2,5-dimethyl-1H-pyrrole-3-carboxylate, 2'-(4-aminophenyl)-1H,1'H-2,5'-bibenzimidazol-5-amine, and salts thereof.

[2] A method for preparing a mature cardiomyocyte, which comprises a step of culturing an immature cardiomyocyte in the presence of the cardiomyocyte maturation promoter of the above-mentioned [1].

[3] A mature cardiomyocyte prepared by the method of the above-mentioned [2].

Effect of the Invention

Since the above-mentioned compounds or salts thereof have an action of maturing cardiomyocytes, they are useful as a cardiomyocyte maturation promoter. The method for promoting cardiomyocyte maturation using the above-mentioned compound matures immature cardiomyocytes in a short period at low cost, as compared with a method for culturing immature cardiomyocytes for a long period.

BRIEF DESCRIPTION OF THE DRAWINGS

FIG. 1 shows the results of mCherry expression analysis by a flow cytometry in Experimental Example 2. The FIGURES show the results in cases of control (no addition), control (DMSO addition) and addition of the compound of Example No. 2, in order from the top.

DETAILED DESCRIPTION OF THE INVENTION

The cardiomyocyte maturation promoter of the present invention comprises one or more compounds selected from the following compounds:
2-methoxy-5-((Z)-2-(3,4,5-trimethoxyphenyl)vinyl)phenol (Example No. 1),
(1-ethyl-1H-benzotriazol-5-yl)methyl (2-(2-methoxy-4-methylphenyl)-4-methyl-1,3-thiazol-5-yl)carbamate (Example No. 2),
(2'beta)-22-oxovincaleukoblastine (Example No. 3), 2-(2-(4-chlorophenyl)ethyl)-6-(2-furyl)-3H-imidazo[4,5-b]pyridine (Example No. 4),
4,5-anhydro-1,2-dideoxy-4-methyl-2-((N-(morpholin-4-ylacetyl)-L-alanyl-O-methyl-L-tyrosyl)amino)-1-phenyl-L-threo-pent-3-ulose (Example No. 5),
3-(3-methoxyphenyl)-N7,N7-dimethylisoquinoline-1,7-diamine (Example No. 6),
methyl 4-(2-benzylbenzoyl)-2,5-dimethyl-1H-pyrrole-3-carboxylate (Example No. 7),
2'-(4-aminophenyl)-1H,1'H-2,5'-bibenzimidazol-5-amine (Example No. 8),
and salts thereof.

When the above-mentioned compound is in the form of a salt, the salt is preferably a pharmacologically acceptable salt, and examples of such salt include a salt with inorganic base, a salt with organic base, a salt with inorganic acid, a salt with organic acid, a salt with basic or acidic amino acid and the like.

Preferable examples of the salt with inorganic base include alkali metal salts such as sodium salt, potassium salt and the like, alkaline earth metal salts such as calcium salt, magnesium salt and the like, aluminum salt, ammonium salt and the like.

Preferable examples of the salt with organic base include salts with trimethylamine, triethylamine, pyridine, picoline, ethanolamine, diethanolamine, triethanolamine, tromethamine[tris(hydroxymethyl)methylamine], tert-butylamine, cyclohexylamine, benzylamine, dicyclohexylamine, N,N-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like. Preferable examples of the salt with acidic amino acid include salts with aspartic acid, glutamic acid and the like.

The cardiomyocyte maturation promoter of the present invention may comprise one or more kind(s) of the above-mentioned compounds or salts thereof.

The above-mentioned compounds or salts thereof can be each produced according to a method known per se, for example, according to the methods described in Patent Documents 3 to 9 and Non-Patent Document 4 or methods analogous thereto.

The above-mentioned compounds may be a hydrate, a non-hydrate, a solvate or a non-solvate.

Furthermore, the above-mentioned compounds may be labeled with or substituted by an isotope (e.g., $^2H$, $^3H$, $^{11}C$, $^{14}C$, $^{18}F$, $^{35}S$, $^{125}I$ etc.) and the like.

Deuteriums conversion form wherein $^1H$ is converted to $^2H(D)$ are also encompassed in the above-mentioned compounds.

Tautomers are also encompassed in the above-mentioned compounds.

The above-mentioned compounds may be a pharmaceutically acceptable cocrystal or cocrystal salt. The cocrystal or cocrystal salt means a crystalline substance constituted with two or more special solids at room temperature, each having different physical properties (e.g., structure, melting point, melting heat, hygroscopicity, solubility and stability). The cocrystal or cocrystal salt can be produced by a cocrystallization method known per se.

The cardiomyocyte maturation promoter of the present invention can be used as it is or by mixing with a pharmacologically acceptable carrier, and formulating the mixture according to a method known per se.

Since the above-mentioned compounds or salts thereof have an excellent activity to promote the maturation of a cardiomyocyte, they are useful as a cardiomyocyte maturation promoter. Therefore, by culturing immature cardiomyocytes in the presence of the above-mentioned compound or a salt thereof, mature cardiomyocytes can be prepared in a shorter period than when culturing in only medium components.

As used herein, the term "pluripotency" means ability to differentiate into various tissues or cells having different morphologies and/or functions, and to differentiate into any series of cells of three germ layers. The "pluripotency" cannot differentiate into blastodisc. Therefore, the "pluripotency" is distinguished from the term "totipotency" which can differentiate into every tissue of the living body including blastodisc, in that it has no ability to form an individual.

As used herein, the term "multipotency" means ability to differentiate into plural limited numbers of series of cells. For example, mesenchymal stem cells, hematopoietic stem cells and neural stem cells are multipotent, but not pluripotent.

As used herein, examples of the "stem cells" include pluripotent stem cells.

The "cardiomyocytes" to which the cardiomyocyte maturation promoter of the present invention is applied is not particularly limited, and they are preferably derived from a mammal (e.g., mouse, rat, hamster, rabbit, cat, dog, cow, sheep, pig, monkey, human), more preferably derived from human.

The cardiomyocytes whose maturation can be promoted by the cardiomyocyte maturation promoter of the present invention are not particularly limited as long as it can be determined that they are in an immature stage based on the below-mentioned marker expression levels, morphologies and structures (e.g., sarcomere, mitochondria), properties (e.g., pulsatility, electrophysiological maturity) and the like.

The cardiomyocytes whose maturation can be promoted by the cardiomyocyte maturation promoter of the present invention may also be cells prepared by differentiation induction from pluripotent stem cells, or immature cardiomyocytes isolated from a living body (e.g., cardiomyocytes derived from a mouse or rat fetus or newborn).

Examples of the pluripotent stem cells include, but are not limited to, embryonic stem (ES) cells, germline stem cells ("GS cells"), embryonic germ cells ("EG cells"), induced pluripotent stem (iPS) cells, embryonic stem cells derived from a cloned embryo obtained by nuclear transfer (ntES cells), and the like. The pluripotent stem cells are preferably ES cells, iPS cells or ntES cells.

(A) Embryonic Stem Cells

ES cells are stem cells established from the inner cell mass of an early embryo (for example, blastocyst) of a mammal such as human, mouse and the like, which cells have pluripotency and growth ability by self-renewal.

ES cells are embryo-derived stem cells originated from the inner cell mass of a blastocyst, which is the embryo formed following the 8-cell stage and the morula stage of a fertilized egg. ES cells have ability to differentiate into any cells constituting an adult, that is, the so-called pluripotency of differentiation, and growth ability by self-renewal. ES cells were discovered in mouse in 1981 (M. J. Evans and M. H. Kaufman (1981), Nature 292: 154-156), and this was followed by establishment of ES cell lines of primates such as human, monkey and the like (J. A. Thomson et al. (1998), Science 282: 1145-1147; J. A. Thomson et al. (1995), Proc. Natl. Acad. Sci. USA, 92: 7844-7848; J. A. Thomson et al. (1996), Biol. Reprod., 55: 254-259; J. A. Thomson and V. S. Marshall (1998), Curr. Top. Dev. Biol., 38: 133-165).

ES cells can be established by removing the inner cell mass from the blastocyst of a fertilized egg of a subject animal, followed by culturing the inner cell mass on feeder fibroblasts. The cells can be maintained by subculture using a culture medium supplemented with a substance(s) such as leukemia inhibitory factor (LIF), basic fibroblast growth factor (bFGF), and the like. Methods of establishment and maintenance of human and monkey ES cells are described in, for example, U.S. Pat. No. 5,843,780 B; Thomson J A, et al. (1995), Proc Natl. Acad. Sci. USA. 92: 7844-7848; Thomson J A, et al. (1998), Science. 282: 1145-1147; H. Suemori et al. (2006), Biochem. Biophys. Res. Commun., 345: 926-932; M. Ueno et al. (2006), Proc. Natl. Acad. Sci. USA, 103: 9554-9559; H. Suemori et al. (2001), Dev. Dyn., 222: 273-279; H. Kawasaki et al. (2002), Proc. Natl. Acad. Sci. USA, 99: 1580-1585; and Klimanskaya I, et al. (2006), Nature. 444: 481-485.

With regard to culture medium for preparation of ES cells, human ES cells can be maintained, for example, using DMEM/F-12 culture medium supplemented with 0.1 mM 2-mercaptoethanol, 0.1 mM non-essential amino acids, 2 mM L-glutamic acid, 20% KSR and 4 ng/ml bFGF at 37° C. under a moist atmosphere of 2% $CO_2$/98% air (O. Fumitaka et al. (2008), Nat. Biotechnol., 26:215-224). ES cells are required to be subcultured every 3 to 4 days, and the subculture can be carried out using, for example, 0.25% trypsin and 0.1 mg/ml collagenase IV in PBS containing 1 mM $CaCl_2$ and 20% KSR.

Selection of ES cells can be generally carried out by the Real-Time PCR method using, as an index, expression of a gene marker such as alkaline phosphatase, Oct-3/4, Nanog and the like. In particular, for selection of human ES cells, expression of a gene marker such as OCT-3/4, NANOG, ECAD and the like can be used as an index (E. Kroon et al. (2008), Nat. Biotechnol., 26: 443-452).

With regard to ES cells, as mouse ES cells, various mouse ES cell lines established by inGenious targeting laboratory, Riken (Institute of Physical and Chemical Research) etc., are available, and, as human ES cells, various human ES cell lines established by NIH, Riken, Kyoto University, Cellartis etc., are available. For examples, examples of human ES cell lines include line CHB-1-CHB-12, line RUES1, line RUES2, line HUES1-HUES28 etc., of NIH, line H1 and line H9 of WisCell Research, and line KhES-1, line KhES-2, line KhES-3, line KhES-4, line KhES-5, line SSES1, line SSES2, line SSES3 etc., of Riken. Alternatively, clinical-grade cell lines, research or clinical cell lines prepared from these cell lines, and the like may be used.

(B) Germline Stem Cells

Germline stem cells are pluripotent stem cells derived from testis, and play a role as the origin for spermatogenesis. Similarly to ES cells, these cells can be induced to differentiate into various series of cells, and, for example, have a property to enable preparation of a chimeric mouse by transplantation of the cells to a mouse blastocyst (M. Kanatsu-Shinohara et al. (2003) Biol. Reprod., 69: 612-616; K. Shinohara et al. (2004), Cell, 119: 1001-1012). Germline stem cells are capable of self-renewal in a culture medium containing glial cell line-derived neurotrophic factor (GDNF), and, by repeating their subculture under the same culture conditions as those for ES cells, germline stem cells can be obtained (Masanori Takehashi et al. (2008), Experimental Medicine, 26(5) (extra edition): 41-46, Yodosha (Tokyo, Japan)).

(C) Embryonic Germ Cells

Embryonic germ cells are established from fetal primordial germ cells and have pluripotency similarly to ES cells. They can be established by culturing primordial germ cells in the presence of substances such as LIF, bFGF, stem cell factor and the like (Y. Matsui et al. (1992), Cell, 70: 841-847; J. L. Resnick et al. (1992), Nature, 359: 550-551).

(D) Induced Pluripotent Stem Cells

The "induced pluripotent stem cell (iPSC)" refers to a cell obtained by introducing a certain factor (nuclear reprogramming factor) into a mammalian somatic cell or an undifferentiated stem cell to perform reprogramming. At present, there are various "induced pluripotent stem cells", and those that can also be used are as follows: an iPSC established by Yamanaka, et al., by introducing four factors, Oct3/4, Sox2, Klf4 and c-Myc into a mouse fibroblast (Takahashi K, Yamanaka S., Cell, (2006) 126: 663-676); as well as an iPSC derived from a human cell established by introducing the same four factors to a human fibroblast (Takahashi K, Yamanaka S., et al. Cell, (2007) 131: 861-872.); a Nanog-iPS cell established by introducing the four factors described above and then performing screening with the expression of Nanog as an index (Okita, K., Ichisaka, T., and Yamanaka, S. (2007). Nature 448, 313-317.); an iPS cell prepared with a method in which c-Myc is not included (Nakagawa M, Yamanaka S., et al. Nature Biotechnology, (2008) 26, 101-106); and an iPS cell established by introducing six factors with a virus free method (Okita K et al. Nat. Methods 2011 May; 8(5):409-12, Okita K et al. Stem Cells. 31(3):458-66). In addition, an induced pluripotent stem cell prepared by Thomson, et al., which is established by introducing four factors, OCT3/4, SOX2, NANOG and LIN28 (Yu J., Thomson J A. et al., Science (2007) 318: 1917-1920.), an induced pluripotent stem cell prepared by Daley, et al. (Park I H, Daley G Q. et al., Nature (2007) 451: 141-146), and an induced pluripotent stem cell prepared by Sakurada, et al. (Japanese Patent Application Laid-Open No. 2008-307007), etc. can also be used.

Besides, any of the induced pluripotent stem cells known so in the art described in all published papers (for example, Shi Y., Ding S., et al., Cell Stem Cell, (2008) Vol 3, Issue 5, 568-574; Kim J B., Scholer H R., et al., Nature, (2008) 454, 646-650; Huangfu D., Melton, D A., et al., Nature Biotechnology, (2008) 26, No 7, 795-797), or patents (for example, Japanese Patent Application Laid-Open No. 2008-307007, Japanese Patent Application Laid-Open No. 2008-283972, US 2008-2336610, US 2009-047263, WO 2007-069666, WO 2008-118220, WO 2008-124133, WO 2008-151058, WO 2009-006930, WO 2009-006997, WO 2009-007852) can also be used.

As induced pluripotent cell lines, various iPSC lines established by NIH, Riken, Kyoto University, etc. are available. For example, examples of human iPSC lines include line HiPS-RIKEN-1A, line HiPS-RIKEN-2A, line HiPS-RIKEN-12A and line Nips-B2 of Riken, line 253G1, line 201B7, line 409B2, line 454E2, line 606A1, line 610B1 and line 648A1 of Kyoto University, and the like. Alternatively, clinical-grade cell lines provided by Kyoto University, Cellular Dynamics International etc., research or clinical cell lines prepared from these cell lines, and the like may be used.

The term "somatic cells" used herein means any animal cells (preferably cells of mammals including human) excluding germ-line cells and totipotent cells such as eggs, oocytes, ES cells and the like. Examples of the somatic cells include, but are not limited to, any of fetal somatic cells, neonatal somatic cells, and mature, healthy or diseased somatic cells, as well as any of primary cultured cells, subcultured cells, and established cell lines. Specific examples of the somatic cells include (1) tissue stem cells (somatic stem cells) such as neural stem cells, hematopoietic stem cells, mesenchymal stem cells, dental pulp stem cells and the like; (2) tissue progenitor cells; (3) differentiated cells such as lymphocytes, epithelial cells, endothelial cells, muscle cells, fibroblasts (skin cells etc.), hair cells, hepatic cells, gastric mucosal cells, enterocytes, spleen cells, pancreatic cells (pancreatic exocrine cells etc.), brain cells, lung cells, kidney cells, adipocytes and the like, and the like.

In the present invention, the mammalian individual from which somatic cells are collected is not limited, and preferably human. In cases where the obtained iPS cells are to be used for human regenerative medicine, it is especially preferred to collect somatic cells from the patient himself or another person having the same or substantially the same human leukocyte antigen (HLA) type in view of prevention of the rejection reaction. Here, "substantially the same" HLA type means that the HLA type is matching to an extent which allows survival of transplanted cells by use of an immunosuppressant(s) and/or the like when cells obtained by differentiation induction from iPS cells derived from the somatic cells are transplanted to the patient. For example, it means that the person has the same major HLAs (for example, at the three gene loci HLA-A, HLA-B and HLA-DR) as those of the patient (the same applies hereinafter). On the other hand, in cases where the cells are not administered (transplanted) to human, for example, in a method for testing toxicity of a candidate drug to cardiomyocytes, the origin of the somatic cells to be used as the source of the iPS cells is not limited. In cases where the iPS cells are used as the source of cells for screening for evaluation of drug sensitivity or side effects of a patient, it is preferred to collect somatic cells from the patient himself or another person who has the same genetic polymorphism(s) associated with the drug sensitivity or the side effects.

(E) ES Cells Derived from Cloned Embryo Obtained by Nuclear Transfer ntES cells are ES cells derived from a cloned embryo prepared by the nuclear transfer technique, and have almost the same properties as those of ES cells derived from fertilized eggs (T. Wakayama et al. (2001), Science, 292: 740-743; S. Wakayama et al. (2005), Biol. Reprod., 72: 932-936; J. Byrne et al. (2007), Nature, 450: 497-502). That is, an ntES (nuclear transfer ES) cell is an ES cell established from the inner cell mass of a blastocyst derived from a cloned embryo obtained by replacement of the nucleus of an unfertilized egg with the nucleus of a somatic cell. For preparation of ntES cells, the combination of the nuclear transfer technique (J. B. Cibelli et al. (1998), Nature Biotechnol., 16: 642-646) and the ES cell preparation technique (described above) is employed (Sayaka Wakayama et al. (2008), Experimental Medicine 26(5) (extra edition), pp. 47-52). In nuclear transfer, reprogramming can be achieved by injecting the nucleus of a somatic cell into a mammalian enucleated unfertilized egg, and culturing the resultant for several hours.

As used herein, the term "cardiomyocyte" means a cell expressing at least one marker gene selected from the group consisting of cardiac troponin (cTNT), αMHC (α myosin heavy chain, MYH6) and βMHC (MYH7). Examples of cTNT include NCBI accession number NM_000364 in a case of human, and NM_001130176 in a case of mouse. Examples of αMHC include NCBI accession number NM_002471 in a case of human, and NM_001164171 in a case of mouse. Examples of βMHC include NCBI accession number NM_000257 in a case of human, and NM_080728 in a case of mouse.

It is known that an isoform switch occurs in which the expression of troponin I1 (TNNI1) is decreased and the expression of troponin I3 (TNNI3) is increased, as cardiomyocytes mature (Fikru B. Bedada, (2014) 3(4): 594-605.). As used herein, "cardiomyocyte is matured (mature)" means that at least TNNI3 expression is increased.

With regard to methods of inducing differentiation of pluripotent stem cells into immature cardiomyocytes, cardiomyocytes can be prepared from pluripotent stem cells by, for example, a method reported by Laflamme M A et al. (Laflamme M A & Murry C E, Nature 2011, Review).

Other examples of the method include, but are not limited to, a method in which cardiomyocytes are prepared by formation of cell mass (embryoid bodies) by suspension culture of induced pluripotent stem cells, a method in which cardiomyocytes are prepared in the presence of a substance that suppresses bone morphogenic protein (BMP) signaling (WO 2005/033298), a method in which cardiomyocytes are prepared by addition of Activin A and BMP in this order (WO 2007/002136), a method in which cardiomyocytes are prepared in the presence of a substance that promotes activation of the canonical Wnt signaling pathway (WO 2007/126077), a method in which Flk/KDR-positive cells are isolated from induced pluripotent stem cells, followed by preparation of cardiomyocytes in the presence of cyclosporin A (WO 2009/118928), and the like.

In addition, a method of inducing differentiation into cardiomyocytes using cytokine by embryoid body formation (Yang L, et al., Human cardiovascular progenitor cells develop from a KDR+ embryonic-stem-cell-derived population., Nature., 2008 May 22; 453(7194):524-8), a method of inducing differentiation into cardiomyocytes by adhesion culture under cytokine-free condition (Lian X, et al., Robust cardiomyocyte differentiation from human pluripotent stem cells via temporal modulation of canonical Wnt signaling., Proc Natl Acad Sci USA., 2012 Jul. 3; 109(27):E1848-57), a method of inducing differentiation into cardiomyocytes by combination use of adhesion culture and suspension culture under cytokine-free condition (Minami I, et al., A small molecule that promotes cardiac differentiation of human pluripotent stem cells under defined, cytokine- and xeno-free conditions., Cell Rep., 2012 Nov. 29; 2(5):1448-60) and the like are also suggested.

The medium to obtain immature cardiomyocytes from pluripotent stem cells is not particularly limited, and mediums known per se can be used. Examples thereof include IMDM medium, Medium 199 medium, Eagle's Minimum Essential Medium (EMEM) medium, αMEM medium, Dulbecco's modified Eagle's Medium (DMEM) medium, Ham's F12 medium, RPMI 1640 medium, Fischer's medium, Neurobasal Medium (Life Technologies), StemPro34 (Invitrogen), medium after removal of solution C from StemFit AK02 (AJINOMOTO AK02, 400 mL of solution A and 100 mL of B solution, total 500 mL), Essential 6 medium (Thermo Fischer Scientific) and mixed media thereof, and the like.

Additives known per se can be added to these mediums, depending on cells and cultural conditions. For example, the medium may contain serum, or may be serum-free. If necessary, the medium may contain one or more of serum replacements such as albumin, transferrin, Knockout Serum Replacement (KSR) (serum replacement for FBS during ES cell culture), N2 supplement (Invitrogen), B27 supplement (Invitrogen), fatty acids, insulin, collagen precursors, trace elements, 2-mercaptoethanol, 1-thiolglycerol and the like, and may also contain one or more of substances such as lipids, amino acids, L-glutamine, Glutamax (Invitrogen), non-essential amino acids, vitamins, growth factors, low-molecular-weight compounds, antibiotics, antioxidants, pyruvic acid, buffers, inorganic salts and the like. Among them, the preferred medium is StemPro34 or a medium after removal of solution C from StemFit AK02, each containing transferrin, 1-thiolglycerol, L-glutamine and ascorbic acid, or RPMI1640 containing B27 supplement.

A combination of activin A, BMP4 and bFGF, or CHIR99021 is used as an initial additive for differentiation induction into cardiomyocytes using the above-mentioned medium.

In the case of the combination of activin A, BMP4 and bFGF, the use concentrations of these additives are preferably 1 ng/ml to 100 ng/ml for activin A, 1 ng/ml to 100 ng/ml for BMP4, and 1 ng/ml to 100 ng/ml for bFGF, more preferably 6 ng/ml for activin A, 10 ng/ml for BMP4, and 5 ng/ml for bFGF.

In the case of CHIR99021, the use concentration is preferably 100 nM to 100 μM, more preferably 4 to 6 μM.

After addition of the above-mentioned additive, by adding vascular endothelial growth factor (VEGF) and a Wnt inhibitor to the medium, the pluripotent stem cells can be differentiated into cardiomyocytes.

The concentration of the VEGF to be used is preferably 1 to 100 ng/ml, more preferably 10 ng/ml.

Examples of the Wnt inhibitor include DKK1 protein (e.g., NCBI accession number:NM_012242 in a case of human), sclerostin (e.g., NCBI accession number: NM_025237 in a case of human), IWR-1 (Merck Millipore), IWP-2 (Sigma-Aldrich), IWP-3 (Sigma-Aldrich), IWP-4 (Sigma-Aldrich), PNU-74654 (Sigma-Aldrich), XAV939 (Sigma-Aldrich) and derivatives thereof, and the like. Among them, IWP-3, IWP-4 and IWR-1 are preferably used.

The concentration of the Wnt inhibitor to be used is not particularly limited as long as it inhibits Wnt, and it is preferably 1 nM to 50 μM, particularly preferably 1 to 2 μM.

The culture period for preparation of immature cardiomyocytes from pluripotent stem cells is, for example, 5 to 365 days, preferably 5 to 100 days, more preferably 5 to 60 days, further more preferably 5 to 40 days, still more preferably 5 to 30 days.

The amount of the compound to be used as the cardiomyocyte maturation promoter of the present invention is not particularly limited, and it is, for example, 0.01 to 100 μM, preferably 0.1 to 30 μM, more preferably 1 to 10 μM, per $1\times10^4$ to $1\times10^7$ cell of immature cardiomyocytes.

As an index of cardiomyocyte maturity, expression level of marker for cardiomyocyte maturation, morphology and structure (e.g., sarcomere, mitochondria), property (e.g., pulsatility, electrophysiological maturity) and the like can be used. These indexes can be confirmed by a method known per se.

For example, the expression level of marker for cardiomyocyte maturation can be analyzed by measuring the expression level of marker gene using PCR; analyzed by the expression level of marker protein using western blot and the like; or analyzed by fluorescent label using microscope or flow cytometry. The index of electrophysiological maturity can be analyzed by the depth of resting membrane potential using patch clamping technique, and the like. The index of sarcomere microstructure or mitochondria can be observed by electronic microscope; analyzed by fluorescent label using microscope or flow cytometry; or function-analyzed by extracellular flux analyzer, and the like.

In one embodiment, the mature cardiomyocytes obtained by using the cardiomyocyte maturation promoter of the present invention can be used in cardiac regenerative medicine. For example, a composition comprising cell mass of the cardiomyocytes prepared by the method of the present invention can be administered to the heart of a patient suffering from cardiac disease. Specifically, the cardiomyocytes obtained by the method of the present invention may be directly transplanted into the heart of a patient suffering from cardiac disease as a cell suspension, or in the form of a cardiomyocyte sheet (single layer or multi layers). For example, WO 2012/133945, WO 2013/137491, WO 2014/192909 and WO 2016/076368 are referred to for the preparation method of cardiomyocyte sheets.

In another embodiment, the cardiomyocytes obtained by using the cardiomyocyte maturation promoter of the present invention can also be used for drug screening or drug cardiotoxicity evaluation for the treatment of cardiac disease, since the cardiomyocytes are homogeneously mature. For example, by administering a test drug to the cardiomyocytes so obtained by the method of the present invention, and then measuring the response of the cardiomyocytes, the effect and toxicity of the test drug can be evaluated.

In another embodiment, the cardiomyocytes with reduced automaticity, which are obtained by using the cardiomyocyte maturation promoter of the present invention, can be used in cardiac regenerative medicine.

EXAMPLES

Experimental Example 1

For detection of cardiomyocyte maturation, double knock-in human iPS cell lines, in which reporter protein sequences, EmGFP (Sequence Number 1) and mCherry (Sequence Number 2) were inserted into gene loci for TNNI1 and TNNI3, respectively, were prepared (the human iPS cells were prepared from episomal vector (loaded gene; OCT3/4, KLF4, SOX2, L-MYC, LIN28, mouse p53DD) using PBMC (LP_167, Sample ID:20130318) purchased from CTL (reference literature; Okita K, et al. Stem Cells. 2012 Nov. 29. doi: 10.1002/stem.1293)).

The maintenance culture of the above-mentioned reporter iPS cell lines was carried out by a conventional method (Okita K, et al. Stem Cells. 2012 Nov. 29. doi: 10.1002/stem.1293).

For differentiation induction into cardiomyocytes, the reporter iPS cell lines were treated with 0.5×TrypLE select (Life Technologies, diluted in ½ with 0.5 mM EDTA/PBS) for 4 to 5 minutes, and the cells were exfoliated using a cell scraper (IWAKI), and then dissociated into the single cell by pipetting. The medium was removed by centrifugation (1,000 rpm, 5 min), and the obtained cells were seeded on a bioreactor (ABLE) by $1 \times 10^7$ cells per 30 mL of the bioreactor, and then cultured in a medium prepared by adding 1% L-glutamine, transferrin 150 µg/mL, ascorbic acid 50 µg/mL (Sigma), monothioglycerol $4 \times 10^{-4}$ M, 10 µM Rock inhibitor (Y-27632), 2 ng/mL BMP4 (R&D) and 0.5% Matrigel (Growth Factor Reduced) to a medium after removal of solution C from StemFit AK02 (AJINOMOTO AK02, 400 mL of solution A and 100 mL of B solution, total 500 mL), at 37° C., under 5% oxygen condition (55 rpm, stirred suspension culture method) to form embryoid bodies (0 day).

Next day (1st day), 9 µL (final concentration 3 ng/mL) of µg/mL activin A, 15 µL (final concentration 5 ng/mL) of 10 µg/mL bFGF and 24 µL (final concentration 10 ng/mL) of 10 µg/mL BMP4 were added to the bioreactor, and the cells were cultured at 37° C. for additional 2 days, under 5% oxygen condition.

Then (3rd day), the obtained embryoid bodies were collected in a 50 mL centrifuge tube, and then subjected to centrifugation (200 g, 1 min). The medium was removed, and the embryoid bodies were cultured in a medium prepared by adding 1% L-glutamine, transferrin 150 µg/mL, ascorbic acid 50 µg/mL (Sigma), monothioglycerol $4 \times 10^{-4}$ M, 10 ng/mL VEGF, 1 µM IWP-3, 0.6 µM dorsomorphin and 5.4 µM SB431542 to a medium after removal of solution C from StemFit AK02 (AJINOMOTO AK02, 400 mL of solution A and 100 mL of B solution, total 500 mL), at 37° C. for 3 days, under 5% oxygen condition (55 rpm, stirred suspension culture method).

Then (6th day), the bioreactor was left to stand to precipitate the embryoid bodies, and 80 to 90% of the medium was removed. A medium prepared by adding 1% L-glutamine, transferrin 150 µg/mL, ascorbic acid 50 µg/mL (Sigma), monothioglycerol $4 \times 10^{-4}$ M and 5 ng/mL VEGF to a medium after removal of solution C from StemFit AK02 (AJINOMOTO AK02, 400 mL of solution A and 100 mL of B solution, total 500 mL) was added to the bioreactor so that the total volume became 30 mL, and the embryoid bodies were cultured for 8 days, at 37° C., under 5% oxygen condition (55 rpm, stirred suspension culture method). During the culture, the medium was replaced with a medium under the same conditions every 2 to 3 days.

14th Day after the start of the differentiation induction, the embryoid bodies were treated with 2 mg/mL collagenase type I (Sigma) for 2 hr, and then with 0.25% trypsin/EDTA (Invitrogen) for 10 min. 50% FBS/IMDM (Thermo Fisher Science) was added thereto, and the embryoid bodies were dissociated into the single cell by pipetting, and then subjected to centrifugation (1,000 rpm, 5 minutes). After the centrifugation, the supernatant was removed, and the cells were re-suspended in a 100 mL of StemFit AK02 medium-based AK02 medium for cardiomyocyte differentiation (prepared by adding ascorbic acid 50 µg/mL, L-glutamine 2 mM, transferrin 150 mg/mL, monothioglycerol $4 \times 10^{-4}$ M and VEGF 5 ng/ml to AJINOMOTO AK02 (400 mL of solution A and 100 mL of B solution, total 500 mL)). The re-suspended cells were seeded on CellCarrier-384 Ultra Microplate (Perkin Elmer/6057300) pre-coated with iMatrix-511 (purchased from Nippi, Inc.) by $1.0 \times 10^4$ cells/well, and cultured in StemFit AK02 medium-based AK02 medium for cardiomyocyte differentiation (prepared by adding ascorbic acid 50 µg/mL, L-glutamine 2 mM, transferrin 150 mg/mL and monothioglycerol $4 \times 10^{-4}$ M to AJINOMOTO AK02 (400 mL of solution A and 100 mL of B solution, total 500 mL) by 70 µL/well).

The test compound (the compounds of Examples No. 1 to 8, shown in the following Table 1, 1 µM, one compound per well) was added to the wells by 50 µL/well on 3rd and 6th culture days. On 8th culture day, the cells were fixed with paraformaldehyde (Wako Pure Chemical Corporation, 163-20145), and subjecting to immunostaining using rat anti-mCherry (Invitrogen, M11217) as a primary antibody and goat anti-rat IgG Alexa 647 (Invitrogen, A-21247) as a secondary antibody. The expression level of Alexa 647 was measured by HCS (high contents screening) system (Perkin Elmer/OperaPhenix High Contents Imaging System) (shooting mode; non-confocal, objective lens; 10×air NAO.3).

The average fluorescent intensity (average of n=60) of control well (no addition of the test compound) was 797, calculated from the measured fluorescent intensities. The results are shown in Table 2 (average of n=3).

TABLE 1

| Ex. No. | IUPAC NAME | Structure | ADDITIVE | MS |
| --- | --- | --- | --- | --- |
| 1 | 2-methoxy-5-((Z)-2-(3,4,5-trimethoxyphenyl)vinyl)phenol | 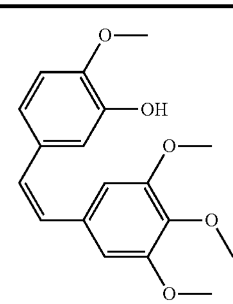 | | 317.2 |

TABLE 1-continued

| Ex. No. | IUPAC NAME | Structure | ADDITIVE | MS |
|---|---|---|---|---|
| 2 | (1-ethyl-1H-benzotriazol-5-yl)methyl(2-(2-methoxy-4-methylphenyl)-4-methyl-1,3-thiazol-5-yl)carbamate | 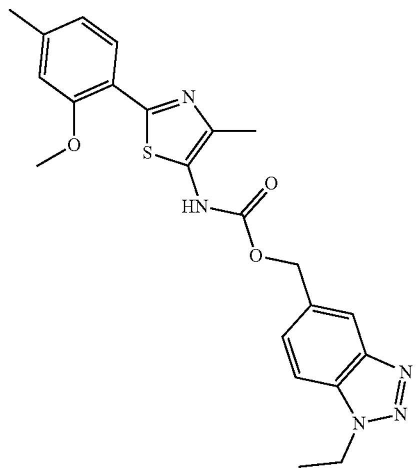 [SMILES: CCn1nnc2cc(COC(=O)Nc3sc(-c4ccc(C)cc4OC)nc3C)ccc21] | | 438.2 |
| 3 | (2'beta)-22-oxovincaleukoblastine | 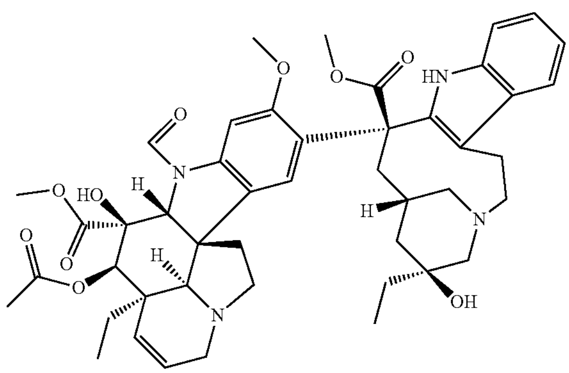 | H2SO4 | 825.3 |
| 4 | 2-(2-(4-chlorophenyl)ethyl)-6-(2-furyl)-3H-imidazo[4,5-b]pyridine | 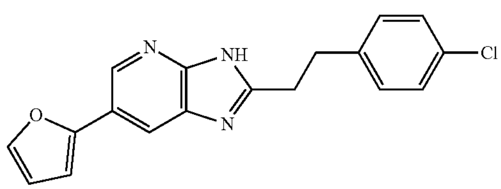 [SMILES: Clc1ccc(CCc2nc3cc(-c4ccco4)cnc3[nH]2)cc1] | | 324.1 |
| 5 | 4,5-anhydro-1,2-dideoxy-4-methyl-2-((N-(morpholin-4-ylacetyl)-L-alanyl-O-methyl-L-tyrosyl)amino)-1-phenyl-L-threo-pent-3-ulose | 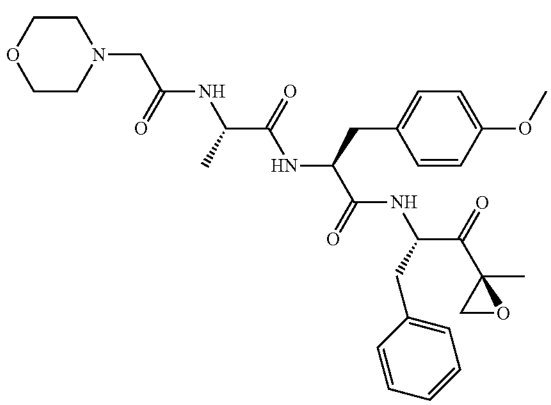 [SMILES: COc1ccc(C[C@H](NC(=O)[C@H](C)NC(=O)CN2CCOCC2)C(=O)N[C@@H](Cc2ccccc2)C(=O)[C@]2(C)CO2)cc1] | | 581.3 |
| 6 | 3-(3-methoxyphenyl)-N7,N7-dimethylisoquinoline-1,7-diamine | 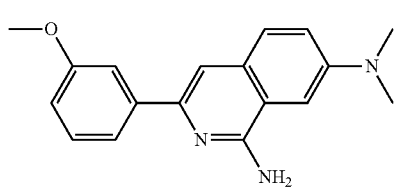 | | 294.0 |

TABLE 1-continued

| Ex. No. | IUPAC NAME | Structure | ADDITIVE | MS |
|---|---|---|---|---|
| 7 | methyl 4-(2-benzylbenzoyl)-2,5-dimethyl-1H-pyrrole-3-carboxylate | 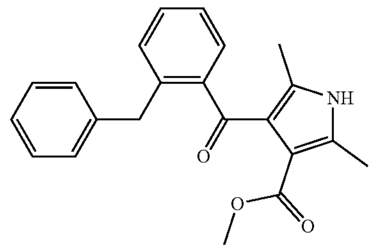 [SMILES: COC(=O)c1c(C)[nH]c(C)c1C(=O)c1ccccc1Cc1ccccc1] | | 348.2 |
| 8 | 2'-(4-aminophenyl)-1H,1'H-2,5'-bibenzimidazol-5-amine | 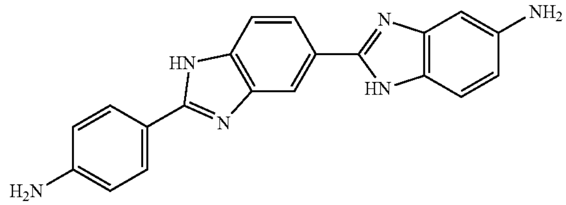 [SMILES: Nc1ccc(-c2nc3cc(-c4nc5cc(N)ccc5[nH]4)ccc3[nH]2)cc1] | | 341.2 |

TABLE 2

| Example No. | average fluorescent intensity (at 1 μM) |
|---|---|
| 1 | 1381 |
| 2 | 1331 |
| 3 | 1710 |
| 4 | 1125 |
| 5 | 1791 |
| 6 | 1305 |
| 7 | 1294 |
| 8 | 1150 |

Experimental Example 2

For detection of cardiomyocyte maturation, double knock-in human iPS cell lines, in which reporter protein sequences, EmGFP (Sequence Number 1) and mCherry (Sequence Number 2) were inserted into gene loci for TNNI1 and TNNI3, respectively, were prepared (the human iPS cells were prepared from episomal vector (loaded gene; OCT3/4, KLF4, SOX2, L-MYC, LIN28, mouse p53DD) using PBMC (LP_167, Sample ID:20130318) purchased from CTL (reference literature; Okita K, et al. Stem Cells. 2012 Nov. 29. doi: 10.1002/stem.1293)).

The maintenance culture of the above-mentioned reporter iPS cell lines was carried out by a conventional method (Okita K, et al. Stem Cells. 2012 Nov. 29. doi: 10.1002/stem.1293).

For differentiation induction into cardiomyocytes, the reporter iPS cell lines were treated with 0.5×TrypLE select (Life Technologies, diluted in ½ with 0.5 mM EDTA/PBS) for 4 to 5 minutes, and the cells were exfoliated using a cell scraper (IWAKI), and then dissociated into the single cell by pipetting. The medium was removed by centrifugation (1,000 rpm, 5 min), and the obtained cells were suspended in a medium prepared by adding 1% L-glutamine, transferrin 150 μg/mL, ascorbic acid 50 μg/mL (Sigma), monothioglycerol $4\times10^{-4}$ M, 10 μM Rock inhibitor (Y-27632), 2 ng/mL BMP4 (R&D) and 0.5% Matrigel (Growth Factor Reduced) to StemPro-34 SFM (ThermoFisher) in a 6 well-plate by $2\times10^6$ cells/1.5 mL/well, and then subjected to static culture at 37° C., under 5% oxygen condition to form embryoid bodies (0 day).

Next day (1st day), a medium prepared by adding 1% L-glutamine, transferrin 150 μg/mL, ascorbic acid 50 μg/mL (Sigma), monothioglycerol $4\times10^{-4}$ M, 1.8 μL (concentration 12 ng/mL) of 10 μg/mL activin A, 15 μL (concentration 10 ng/mL) of μg/mL bFGF and 2.7 μL (concentration 18 ng/mL) of 10 μg/mL BMP4 to 1.5 mL of StemPro-34 SFM (ThermoFisher) was added to each well of the 6 well plate containing the embryoid bodies to adjust the volume combined with the 0 day's medium to final 3 mL (activin A: 6 ng/ml, bFGF: 5 ng/ml, BMP4: 10 ng/ml), and the embryoid bodies were cultured at 37° C. for additional 2 days, under 5% oxygen condition.

Then (3rd day), the 6 well plate containing the embryoid bodies was inclined, and then left to stand for 1 to 2 minutes until the embryoid bodies were precipitated at the edges of the wells, and the supernatant was aspirated so as not to suck the embryoid bodies. Then, IMDM (ThermoFisher) medium was added to each well, and, as above, the plate was inclined, and then left to stand for 1 to 2 minutes, and the supernatant was aspirated so as not to suck the embryoid bodies. A medium prepared by adding 1% L-glutamine, transferrin 150 μg/mL, ascorbic acid 50 μg/mL (Sigma), monothioglycerol $4\times10^{-4}$ M, 10 ng/mL VEGF, 1 μM IWP-3, 0.6 μM dorsomorphin and 5.4 μM SB431542 to 3 mL of StemPro-34 SFM (ThermoFisher) was added to each well of the 6 well plate, and then the embryoid bodies were cultured at 37° C. for 3 days, under 5% oxygen condition.

Then (6th day), the 6 well plate containing the embryoid bodies was inclined, and then left to stand for 1 to 2 minutes until the embryoid bodies were precipitated at the edges of the wells, and the supernatant was aspirated so as not to suck the embryoid bodies. A medium prepared by adding 1% L-glutamine, transferrin 150 μg/mL, ascorbic acid 50 μg/mL (Sigma), monothioglycerol $4\times10^{-4}$ M and 5 ng/mL VEGF to 2 mL of StemPro-34 SFM (ThermoFisher) was added to each well of the 6 well plate, and then the embryoid bodies were cultured at 37° C. for 4 days, under 5% oxygen condition. On 8th day, the medium was replaced with a medium under the same conditions.

Then (10th day), the 6 well plate containing the embryoid bodies was inclined, and then left to stand for 1 to 2 minutes until the embryoid bodies were precipitated at the edges of the wells, and the supernatant was aspirated so as not to suck the embryoid bodies. A medium prepared by adding (1) 1% L-glutamine, transferrin 150 μg/mL, ascorbic acid 50 μg/mL (Sigma), monothioglycerol $4 \times 10^{-4}$ M and 5 ng/mL VEGF, and (2) 40 nM of the compound of Example No. 2 or DMSO (0.1% addition relative to the medium volume) to 2 mL of StemPro-34 SFM (ThermoFisher) was added to each well of the 6 well plate, and then the embryoid bodies were cultured at 37° C. for 6 days, under general oxygen condition. On 13th day, the medium was replaced with a medium under the same conditions.

On the 16th day, after the embryoid bodies under each condition were photographed by fluorescence microscope, the 6 well plate containing the embryoid bodies was inclined, and then left to stand for 1 to 2 minutes until the embryoid bodies were precipitated at the edges of the wells, and the supernatant was aspirated so as not to suck the embryoid bodies. Then, 2 mL of PBS was added to each well, and, as so above, the plate was inclined, and then left to stand for 1 to 2 minutes, and the PBS was aspirated so as not to suck the embryoid bodies. A solution prepared by adding DNase 10 μg/mL and Liberase 100 μg/mL to 3 mL of IMDM was added to each well, and the plate was left to stand at 37° C. for 1 hr, under general oxygen condition. After 1 hr, the plate was inclined, and then left to stand for 1 to 2 minutes until the embryoid bodies were precipitated at the edges of the wells, and the supernatant was aspirated so as not to suck the embryoid bodies. Then, 2 mL of PBS was added to each well, and, as above, the plate was inclined, and then left to stand for 1 to 2 minutes, and the PBS was aspirated so as not to suck the embryoid bodies. A solution prepared by adding DNase 10 μg/mL to 2 mL of TrypLE select was added to each well, and the plate was left to stand at 37° C. for 10 minutes, under general oxygen condition. Then, a medium prepared by adding 1% L-glutamine, transferrin 150 μg/mL, ascorbic acid 50 μg/mL (Sigma), monothioglycerol $4 \times 10^{-4}$ M, 5 ng/mL VEGF and DNase 10 μg/mL to 2 mL of StemPro-34 SFM (ThermoFisher) was added to each well, and the embryoid bodies were dissociated into the single cell by pipetting, and then subjected to centrifugation (1,000 rpm, 5 minutes). After the centrifugation, the supernatant was removed, the cells were suspended in 1 to 2 mL of 2% FBS/PBS, and the mCherry expression in TNNI1$^+$ cells was analyzed by flow cytometry (BD FACSAria Fusion cell sorter). The results are shown in Table 3 and FIG. 1.

TABLE 3

|  | mCherry$^+$ (%) |
|---|---|
| control (addition of (1) alone) | 7.4 |
| control (0.1% DMSO addition relative to the medium volume) | 10.2 |
| Example No. 2 40 nM | 36.1 |

INDUSTRIAL APPLICABILITY

Since the above-mentioned compounds or salts thereof have an activity to promote the maturation of a cardiomyocyte, they are useful as a cardiomyocyte maturation promoter.

This application is based on patent application No. 2018-69871 filed on Mar. 30, 2018 in Japan, the contents of which are encompassed in full herein.

The invention claimed is:

1. A cardiomyocyte maturation promoter comprising at least one compound selected from 2-methoxy-5-((Z)-2-(3,4,5-trimethoxyphenyl)vinyl)phenol, (1-ethyl-1H-benzotriazol-5-yl)methyl (2-(2-methoxy-4-methylphenyl)-4-methyl-1,3-thiazol-5-yl)carbamate, (2'beta)-22-oxovincaleukoblastine, 2-(2-(4-chlorophenyl)ethyl)-6-(2-furyl)-3H-imidazo[4,5-b]pyridine, 4,5-anhydro-1,2-dideoxy-4-methyl-24N-(morpholin-4-ylacetyl)-L-alanyl-O-methyl-L-tyrosyl)amino)-1-phenyl-L-threo-pent-3-ulose, 3-(3-methoxyphenyl)-N7,N7-dimethylisoquinoline-1,7-diamine, methyl 4-(2-benzylbenzoyl)-2,5-dimethyl-1H-pyrrole-3-carboxylate, 2'-(4-aminophenyl)-1H,1'H-2,5'-bibenzimidazol-5-amine, and salts thereof.

2. A method for preparing a mature cardiomyocyte, which comprises a step of culturing an immature cardiomyocyte in the presence of the cardiomyocyte maturation promoter according to claim 1.

* * * * *

SEQUENCE LISTING

```
<160> NUMBER OF SEQ ID NOS: 2

<210> SEQ ID NO 1
<211> LENGTH: 720
<212> TYPE: DNA
<213> ORGANISM: Artificial Sequence
<220> FEATURE:
<223> OTHER INFORMATION: Emerald Green Fluorescent Protein (EmGFP)

<400> SEQUENCE: 1
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccttcaccta cggcgtgcag tgcttcgccc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaag gtctatatca ccgccgacaa gcagaagaac     480
ggcatcaagg tgaacttcaa gacccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720
```

```
<210> SEQ ID NO 2
<211> LENGTH: 711
<212> TYPE: DNA
<213> ORGANISM: Artificial Sequence
<220> FEATURE:
<223> OTHER INFORMATION: mCherry

<400> SEQUENCE: 2
atggtgagca agggcgagga ggataacatg gccatcatca aggagttcat gcgcttcaag      60
gtgcacatgg agggctccgt gaacggccac gagttcgaga tcgagggcga gggcgagggc     120
cgcccctacg agggcaccca gaccgccaag ctgaaggtga ccaagggtgg ccccctgccc     180
ttcgcctggg acatcctgtc ccctcagttc atgtacggct ccaaggccta cgtgaagcac     240
cccgccgaca tccccgacta cttgaagctg tccttccccg agggcttcaa gtgggagcgc     300
gtgatgaact tcgaggacgg cggcgtggtg accgtgaccc aggactcctc cctgcaggac     360
ggcgagttca tctacaaggt gaagctgcgc ggcaccaact tccctccga cggccccgta      420 atgcagaaga agaccatggg ctgggaggcc tcctccgagc ggatgtaccc cgaggacggc     480
gccctgaagg gcgagatcaa gcagaggctg aagctgaagg acggcggcca ctacgacgct     540
gaggtcaaga ccacctacaa ggccaagaag cccgtgcagc tgcccggcgc ctacaacgtc     600
aacatcaagt tggacatcac ctcccacaac gaggactaca ccatcgtgga acagtacgaa     660
cgcgccgagg ccgccactc caccggcggc atggacgagc tgtacaagta g               711
```